United States Patent
Libinson et al.

(10) Patent No.: US 6,943,898 B2
(45) Date of Patent: Sep. 13, 2005

(54) APPARATUS AND METHOD FOR DUAL SPOT INSPECTION OF REPETITIVE PATTERNS

(75) Inventors: Alexander Libinson, Holon (IL); Haim Feldman, Nof Ayalon (IL); Daniel Some, Ashdod (IL); Boris Goldberg, Ashdod (IL)

(73) Assignee: Applied Materials Israel, Ltd., Rehovot (IL)

( * ) Notice: Subject to any disclaimer, the term of this patent is extended or adjusted under 35 U.S.C. 154(b) by 251 days.

(21) Appl. No.: 10/353,754

(22) Filed: Jan. 28, 2003

(65) Prior Publication Data

US 2003/0210402 A1 Nov. 13, 2003

Related U.S. Application Data

(63) Continuation-in-part of application No. 10/141,632, filed on May 7, 2002, now abandoned.

(51) Int. Cl.[7] ................................................. G01B 9/02
(52) U.S. Cl. ........................................................ 356/516
(58) Field of Search ............................... 356/511, 516, 356/489

(56) References Cited

U.S. PATENT DOCUMENTS

| | | | | | |
|---|---|---|---|---|---|
| 3,796,495 A | * | 3/1974 | Laub | .......................... | 356/516 |
| 3,851,951 A | * | 12/1974 | Eveleth | ...................... | 359/286 |
| 4,627,730 A | * | 12/1986 | Jungerman et al. | ......... | 356/516 |
| 4,650,330 A | * | 3/1987 | Fujita | .......................... | 356/516 |

* cited by examiner

*Primary Examiner*—Samuel A. Turner
(74) *Attorney, Agent, or Firm*—Blakely, Sokoloff Taylor & Zafman

(57) ABSTRACT

Apparatus for optical assessment of a sample includes a radiation source, adapted to generate a beam of coherent radiation, and traveling lens optics, adapted to focus the beam so as to generate first and second spots on a surface of the sample and to scan the spots together over the surface. The distance between the first and second spots is responsive to a pitch of a repetitive pattern of the sample. Collection optics are positioned to collect the radiation scattered from the first and second spots and to focus the collected radiation so as to generate an interference pattern. A detector detects a change in the interference pattern.

18 Claims, 10 Drawing Sheets

85

87

84

BEAM STOP 82"

US 6,943,898 B2

APPARATUS AND METHOD FOR DUAL SPOT INSPECTION OF REPETITIVE PATTERNS

RELATED APPLICATIONS

The application is a Continuation In Part of U.S. patent application Ser. No. 10/141,632 Filed May 7, 2002, now abandoned.

FIELD OF THE INVENTION

The present invention relates generally to laser scanning systems, and specifically to methods and systems for optical inspection of objects that have repetitive patterns, such as integrated circuits, wafers, masks, and other objects based on coherent radiation scanning.

BACKGROUND OF THE INVENTION

It is known in the art of microscopy to observe phase variations in an image of a sample in order to enhance detection of features that would otherwise be difficult to see. For example, methods of differential interference contrast (DIC) microscopy are described by M. Bass, E. W. Van Stryland, D. R. Williams, W. L. Wolfe in HandBook of Optics II (Second Edition, McGraw Hill, 1995), pages 17.28–17.36, which are incorporated herein by reference. DIC microscopy provides a shadow cast image that effectively displays the gradient of optical paths. Those regions of the sample where the optical paths increase along a certain reference direction appear brighter, while those where the path differences decrease appears in reverse contrast. Image contrast is greater the steeper the gradient of path differences. DIC methods are useful for highlighting features such as very thin filaments and sharp interfaces, and show differences in local refractive index, as well as changes in surface elevation.

Traveling lens acousto-optic devices are also known in the art. A device of this sort is described, for example, by Eveleth in U.S. Pat. No. 3,851,951, whose disclosure is incorporated herein by reference. An acoustic transducer is coupled to one end of an acousto-optic Bragg cell. The acoustic transducer generates frequency-modulated acoustic pulses in the Bragg cell, which travel from one end of the cell to the other. The resulting spatial frequency variation of the traveling acoustic pulse causes a laser beam that passes through the pulse area to be focused onto an image plane. As the acoustic pulse travels from one end of the Bragg cell to the other, it acts as a traveling lens, causing the focused laser spot to be scanned across the image plane.

It is known in the art that when a patterned object, such as a wafer, mask and the like, is illuminated with coherent radiation spots, such as but not limited to light spots, whereas each light spot is relatively large in relation to the repetitive pattern period, the coherent light is diffracted from the repetitive pattern and generates an interference pattern that is characterized by constructive interference lobes along well defined directions. The position and extent of the interference lobes depend on the period of the repetitive pattern, as well as the wavelength of the incident radiation and characteristics of the optical system. These interference lobes (also termed bright fringes) may prevent the detection of defects, either by masking scattered light from defects, by saturating the detector or by reducing the inspection system sensitivity to light scattered from defects.

SUMMARY OF THE INVENTION

It is an object of some aspects of the present invention to provide improved methods and systems for optical inspection of a sample by laser scanning.

In some embodiments of the present invention, a traveling lens device is used to focus a laser beam so as to generate and scan a pair of closely spaced focal spots across the surface of a sample that includes a repetitive pattern. The spots are spaced apart by a distance that is responsive to a pitch of the repetitive pattern. Preferably, the spots are spaced apart by a multiple integer of said pitch. Preferably, the traveling lens device comprises an acousto-optic Bragg cell, as described above, and the two focal spots are created by generating two closely-spaced (typically overlapping) acoustic pulses, which travel through the Bragg cell together.

Light scattered from the two spots on the surface of the sample create an interference pattern, wherein the position of the interference pattern fringes, as well as the interference pattern intensity distribution vary in response to defects. The interference pattern may be roughly divided to dark fringes and bright fringes, the centers of the dark fringes correspond to minima of the interference pattern, while the centers of the bright fringes correspond to maxima of the interference pattern.

Defects, such as scratches, holes, cavities, particles, and the like that may result in reflectivity changes, height changes and other disorders may affect the location as well as the intensity of the dark and bright fringes. According to an aspect of the invention the location as well as the intensity of at the interference pattern, and especially a minimum value of said interference pattern are measured to provide an indication of a possible defect.

According to an aspect of the invention a detector and a beam stop are located such as to define a detection zone that corresponds to a location of at least one estimated dark fringe. It is noted that the detection zone may correspond to the locations of multiple estimated dark fringes, and may be adjusted to distinct interference patterns resulting from distinct repetitive patterns of an inspected wafer and/or distinct locations of the detector and beam stop in relation to the sample.

According to further embodiments of the invention multiple detectors may be positioned at various locations to define multiple collection zones, thus providing more information about the interference patterns and accordingly to facilitate improved defect detection capabilities. At least some of the detectors may be positioned (and the beam stop may be configured) to detect bright fringes. These detectors may have distinct sensitivity and/or dynamic range than the detectors that are designed to collect dark fringes.

Once the interference pattern is estimated (either by calculation or by measurement or by a combination of both), usually assuming a non-defective wafer, a detector and a beam stop may be positioned such as to define a collection zone. It is noted that the measurement may be performed when the first and second spot interact with a repetitive pattern of the wafer. If is further noted that multiple measurements iteration may be executed to provide a better/finer estimation of the interference pattern. Changes of the dark fringe intensity as well as displacement of the dark fringe may indicate the presence of a defect. Especially, the intensity of signals detected by the detector are expected to increase at the presence of a defect as the minima intensity rises and/or the interference pattern shifts thus exposing the detector to higher intensity portions of the interference pattern.

Both detector and beam stop are preceded by collection optics for collecting light scattered from the inspected wafer and directing it to the beam stop and detector. According to an aspect of the invention the beam stop is positioned such as to receive a conjugate image of the exit pupil of the collecting optics such that the location of the dark fringes does not alter as a result of scanning the wafer. It is noted that the beam stop may form a part of the collection optics, but this is not necessarily so.

In a preferred embodiment, the traveling lens optics include an acousto-optic Bragg cell and an acoustic transducer coupled to the cell so as to produce a frequency-modulated acoustic pulse, which travels along a length of the cell, such that when the beam of radiation passes through the cell, it is focused and scanned by the acoustic pulse, and an optical splitter, which is configured to split the beam that is focused and scanned by the acoustic pulse in the Bragg cell, so as to generate the first and second spots on the surface.

According to yet a further aspect of the invention the size of each spot is relatively small in relation to the pitch of the repetitive pattern. This facilitates high resolution (as the spots are small), whereas the distance between the spots facilitates interference-based inspection. The "size" of the spot may be defined as the spot's diameter, or in cases of non-circular spots, the size of the spot's projection along an axis that connects the first and the second spots.

It is noted that the size of the spots may be equal to or even greater than the pitch, but smaller spots contributes to the resolution of the inspection system.

BRIEF DESCRIPTION OF THE DRAWINGS

The present invention will be more fully understood from the following detailed description of the preferred embodiments thereof, taken together with the drawings in which.

DETAILED DESCRIPTION OF PREFERRED EMBODIMENTS

Figure 1A:
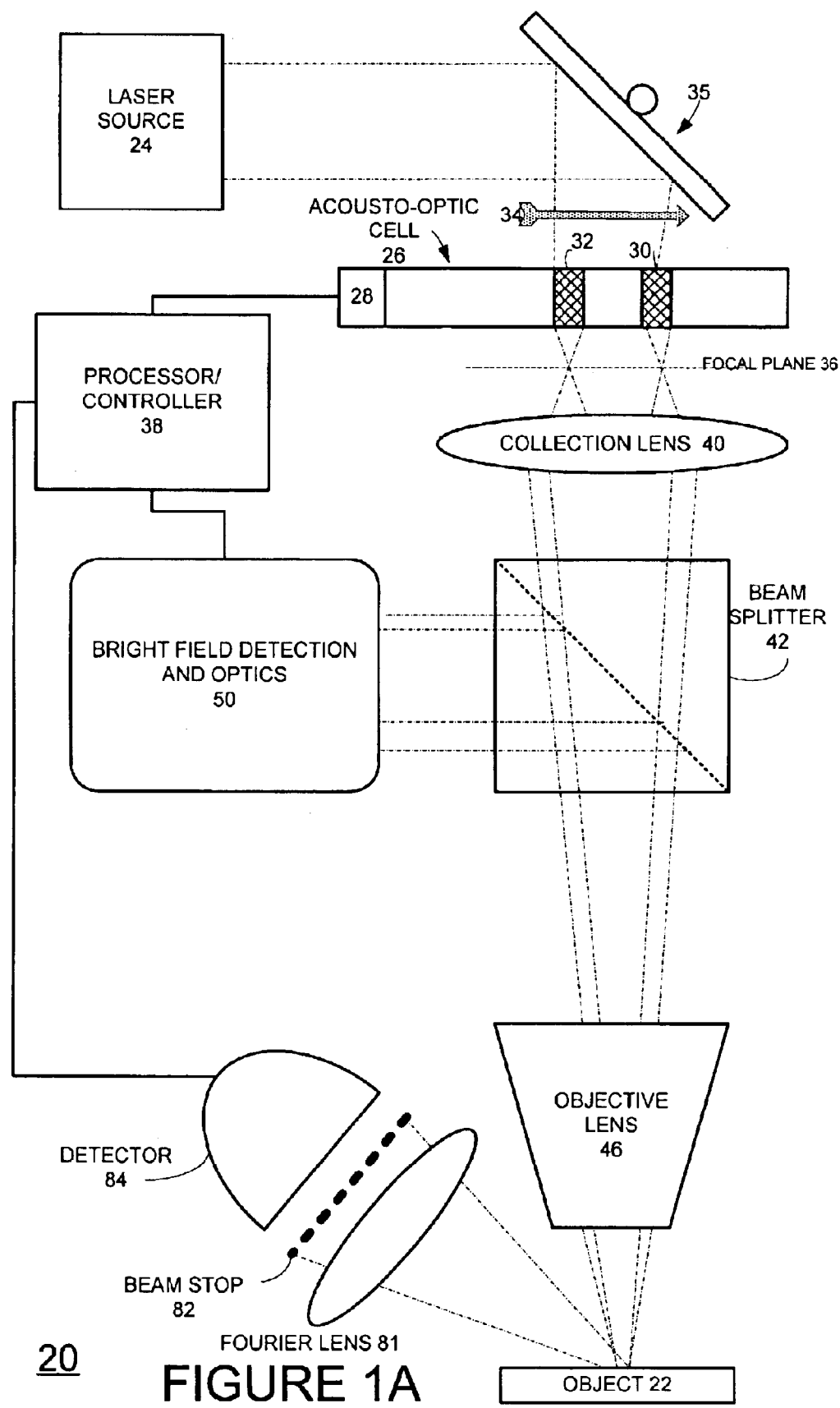
FIGS. 1A–1C and 4 are schematic side views of a dual-spot optical scanning and detection system, in accordance with embodiments of the present invention.

FIG. 1A is a schematic side view of a dual-spot optical scanning and detection system 20, in accordance with a preferred embodiment of the present invention. This system is typically used in automated, high-speed inspection of a sample 22, such as a semiconductor wafer. Alternatively, the principles embodied in system 20 may be applied in other areas of optical imaging, both in the reflective mode shown in the figures and in transmissive modes, as are known in the art. Systems of this sort are useful particularly in observing defects and pattern variations in semiconductor wafers and photomasks, as well as in other applications of optical phase-based detection, such as in scanning microscopy, including particularly confocal microscopy.

Radiation source, such as laser source 24 outputs a laser beam, which is directed to pass through an acousto-optic Bragg cell 26. An acoustic transducer 28 applies two acoustic pulses to cell 26 in close succession, causing two traveling lenses 30 and 32 to travel from one end of the cell to the other, as indicated by an arrow 34. Preferably, cell 26 comprises a material that exhibits a strong acoustic effect on refractive index and weak acoustic attenuation, such as $TeO_2$, $LiNbO_3$, $SiO_2$ or $H_2O$, or other materials known in the art. Each of the two lenses focuses the laser beam to a respective spot in a focal plane 36. As lenses 30 and 32 travel through cell 26, these two spots scan rapidly along a line in the focal plane. Because the acousto-optic effect is linear, the two traveling lenses can overlap without substantially affecting the focusing properties of either lens. The spot separation can be controlled by varying the relative timing of the acoustic pulses used to create traveling lenses 30 and 32.

Optionally, the laser beam from source 24 is scanned over cell 26 by a pre-scanner 35, such as a scanning mirror or another acousto-optic cell, so that the laser beam tracks the traveling lenses.

Figure 1B:
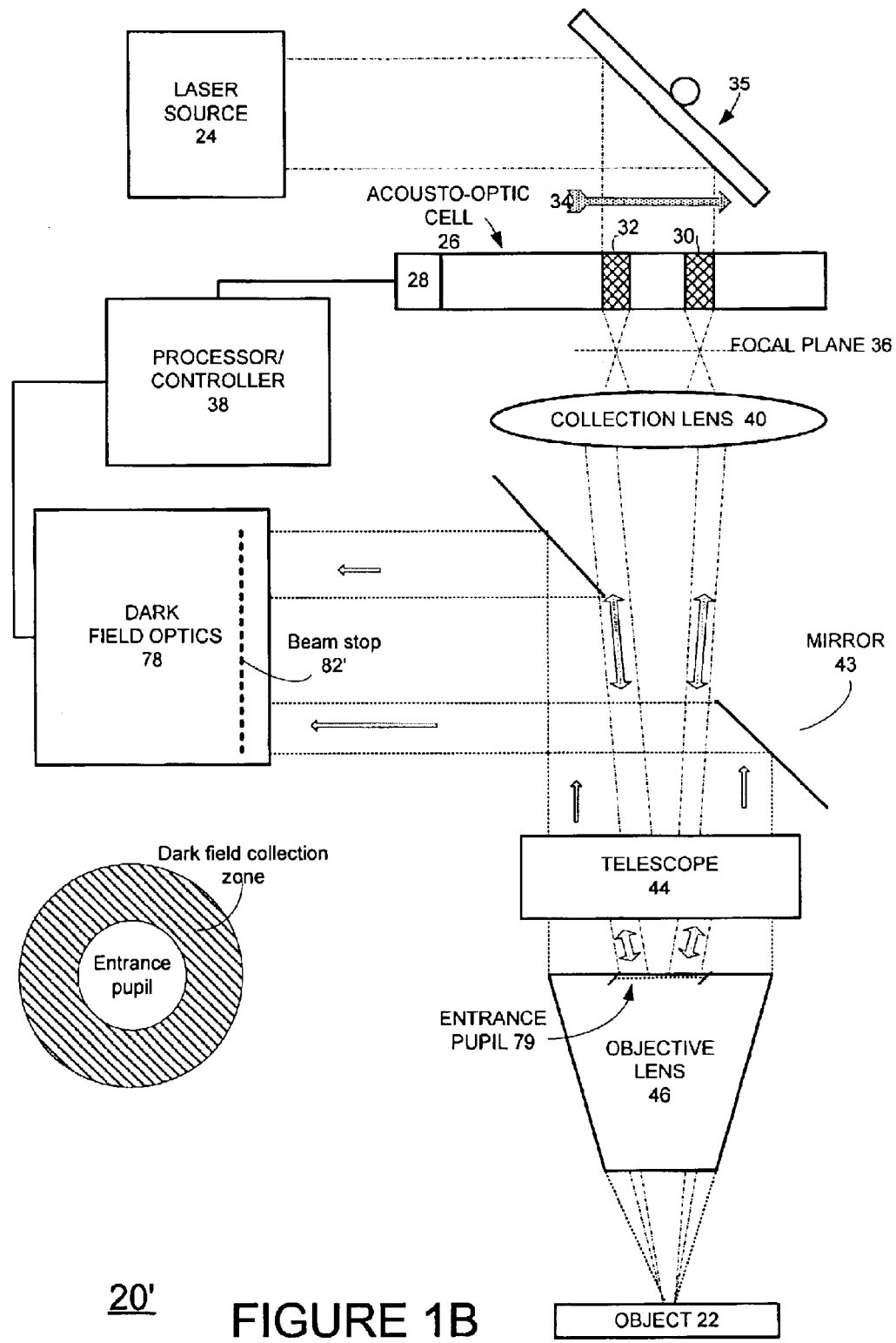
Figure 1C:
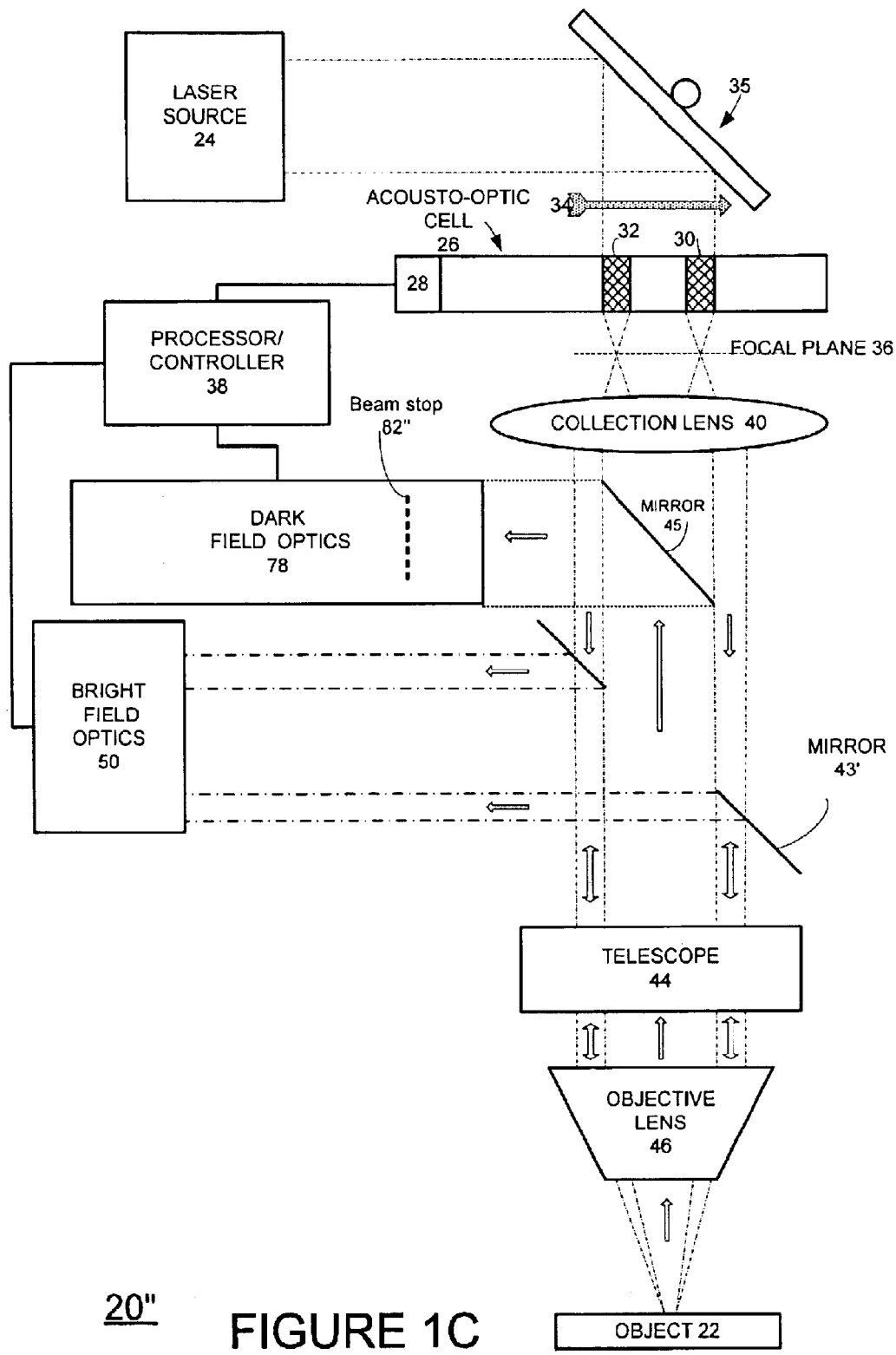

A collection lens 40 collects the light from focal plane 36 and directs it through beam-splitter 42 towards optional telescope (not shown in FIG. 1A) and objective lens 46. Collection lens 40 and objective lens 46 are positioned such that the scanned beams are directed to an effective entrance pupil (not shown) of objective lens 46. In FIGS. 1B–1C the effective entrance pupil (denoted 79) is smaller than the objective lens thus facilitating dark field detection. Telescope 44 and objective lens 46 then focus the light so as to create two spots 48 and 50 on the surface of sample 22.

Referring back to FIG. 1A, collection optics such as Fourier lens 81 collects the light scattered from the two spots, creating an interference pattern that is in focus at beam stop 82. Beam stop 82 is positioned at a Fourier plane defined by Fourier lens 81. Light that passes through beam stop 82 is detected by a detection unit, such as detector 84 and processor 38.

Referring to FIG. 1B illustrating system 20', in accordance with another embodiment of the invention. System 20' has a collection optics that includes objective lens 46, telescope 44, mirror 43 and dark field optics 78. Mirror 43 has an inner transparent portion through which beams from collection lens 40 may propagate towards telescope 44. Mirror 43 also has an oblique and reflective annular portion for reflecting dark field components of scattered light towards dark field optics.

Referring to FIG. 1C illustrating system 20", in accordance with a further embodiment of the invention. System 20" has a collection optics that includes objective lens 46, telescope 44, mirror 45, annular mirror 43' and dark field optics 78. Annular mirror 43 defines an inner transparent circle that is surrounded by a ring. The ring passes light through its upper surface but reflects light from its lower surface. Mirror 45 is positioned in correspondence to the inner transparent circle such as to reflect dark field light passing through the inner transparent circle towards dark field optics 78 that includes beam stop 82".

The shape of the interference pattern, and especially the shape of the dark and bright fringes are responsive to the relative displacement between the illumination and collection light paths. In system 20 of FIG. 14 the dark and bright fringes are arc-shaped. In systems 20' and 20" of FIGS. 1A and 1B the dark fringes and bright fringes appear as straight lines.

Systems 20' and 20" of FIGS. 1B and 1C include dark field optics 78 that are arranged to produce, at beam stops 82' and 82" respectively, a conjugate image of the exit pupil of objective lens 46, at which the interference pattern is again in focus. Dark field optics 78 may include relay lenses, telescopes and detectors.

Referring to FIGS. 1A–1C, Light scattered from the two spots on the surface of sample 20 create an interference pattern, wherein the position of the interference pattern fringes, as well as the interference pattern intensity distribution vary in response to defects.

Figure 2A:
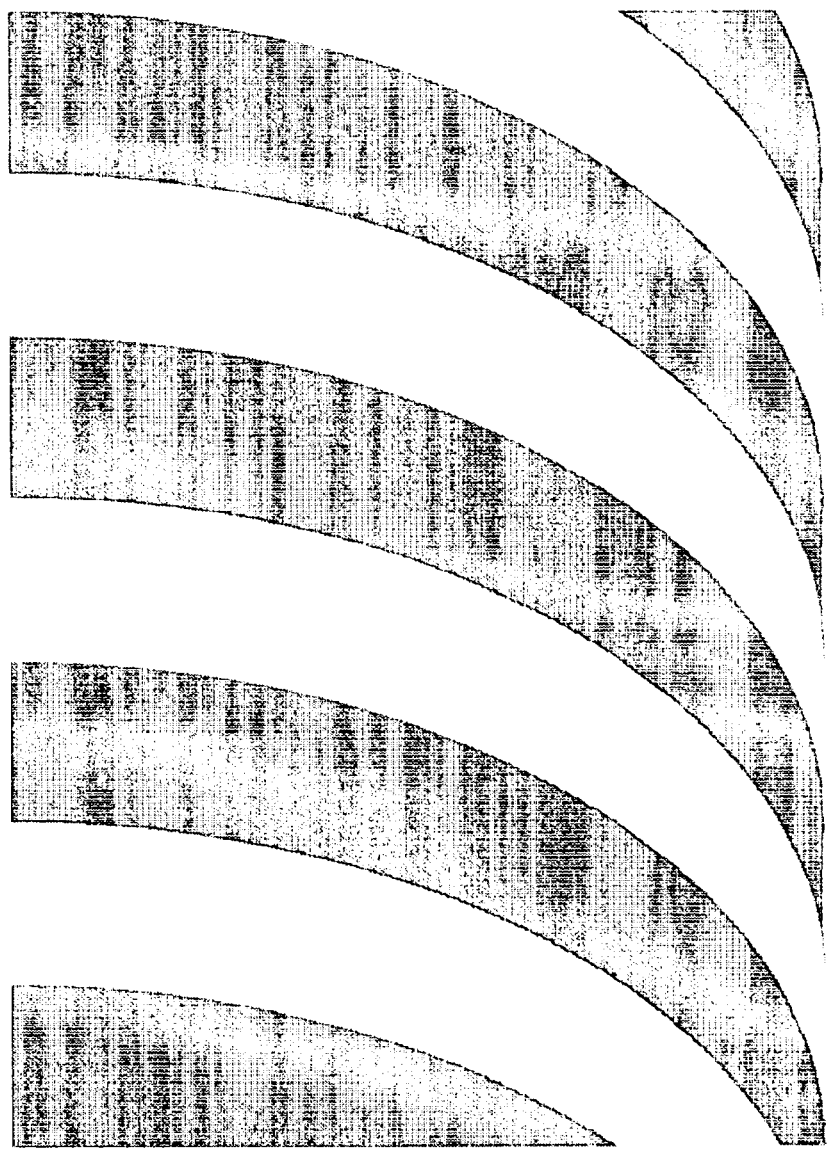
FIGS. 2A–2B are schematic illustrations of interference patterns resulting from non-defective repetitive pattern, in accordance with embodiments of the present invention.
Figure 2B:
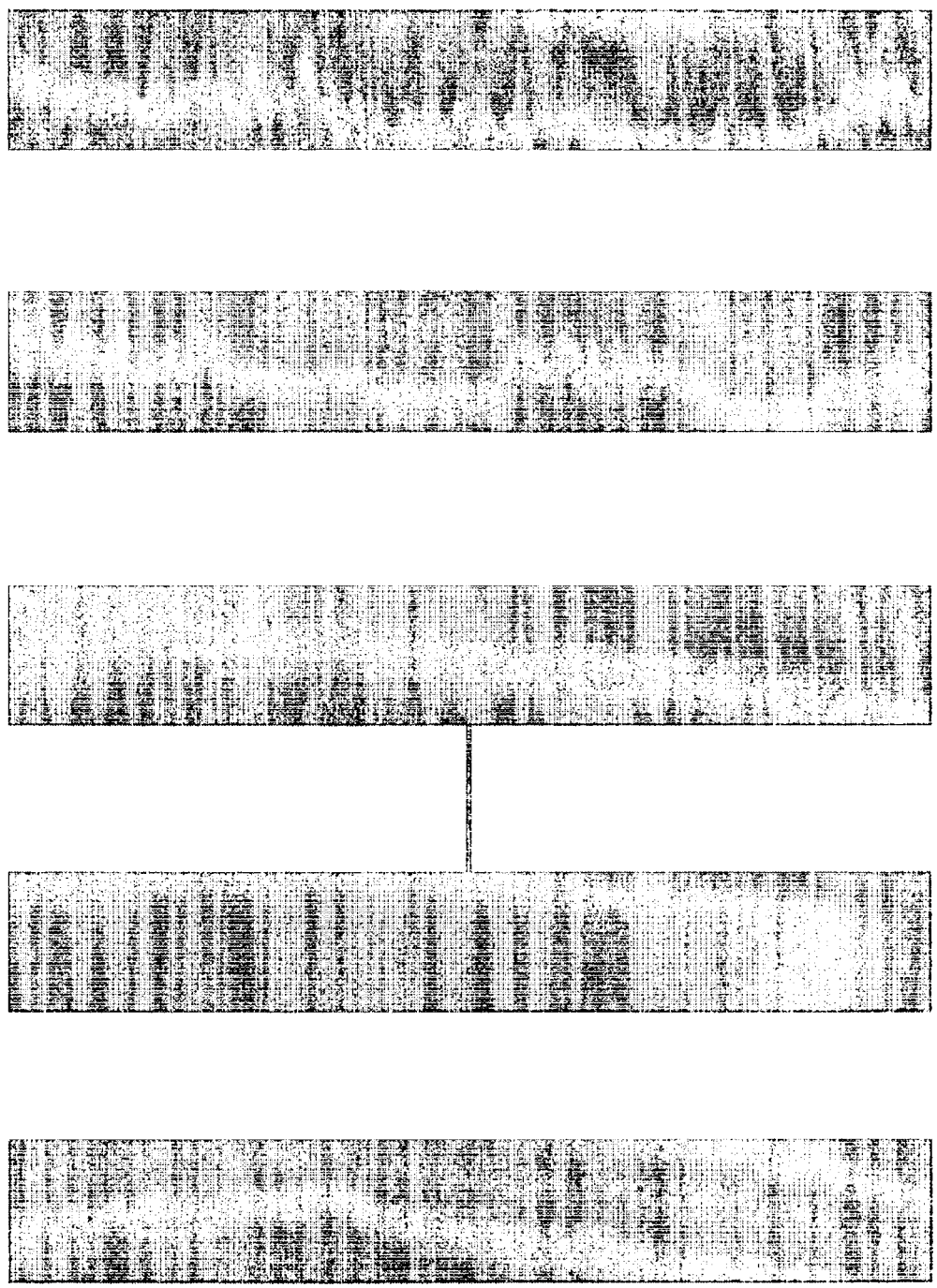

FIG. 2A illustrates the interference pattern 85 resulting from non-defective repetitive pattern of object 22 that appears at beam stop 82 of FIG. 1A, while the interference pattern 87 that appears at beam stops 82' and 82" is illustrated at FIG. 2B.

The interference pattern may be roughly divided to dark fringes and bright fringes, the centers of the dark fringes correspond to minima of the interference pattern, while the centers of the bright fringes correspond to maxima of the interference pattern.

Defects, such as scratches, holes, cavities, particles, and the like that may cause reflectivity changes, height change and other disorders may affect the location as well as the intensity of the dark and bright fringes. According to an aspect of the invention the location as well as the intensity of at the interference pattern, and especially a minimum value of said interference pattern are measured to provide an indication of a possible defect.

Detector 84 and a beam stop 82 of FIG. 1A (as well as corresponding beam stops and detectors of FIGS. 1B and 1C) are located such as to define a detection zone that corresponds to a location of at least one estimated dark fringe. It is noted that the detection zone may correspond to the locations of multiple estimated dark fringes, and may be adjusted to distinct interference patterns resulting from distinct repetitive patterns of an inspected wafer and/or distinct locations of the detector and beam stop in relation to the sample. It is noted that the collection zone may respond to portions of said fringes.

Figure 3A:
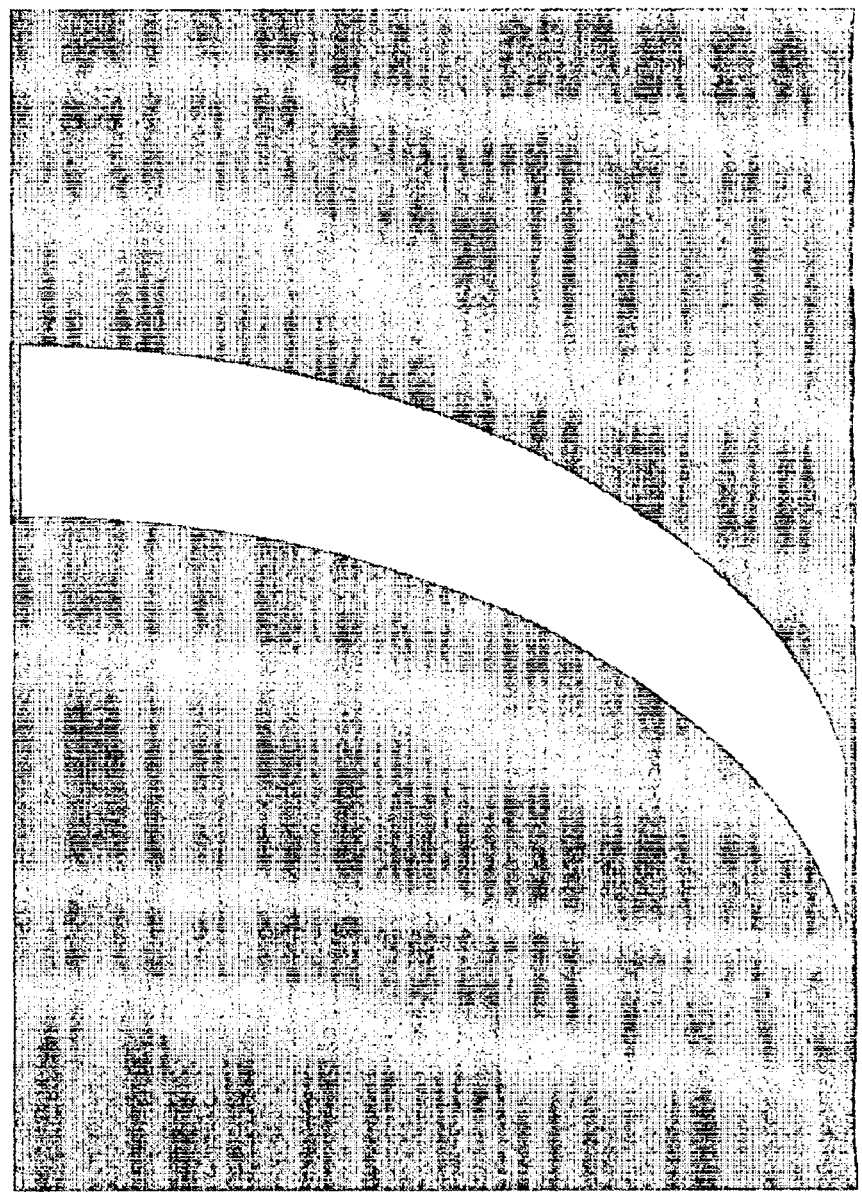
FIGS. 3A–3C are schematic illustrations of beam stops, in accordance with embodiments of the invention.
Figure 3B:
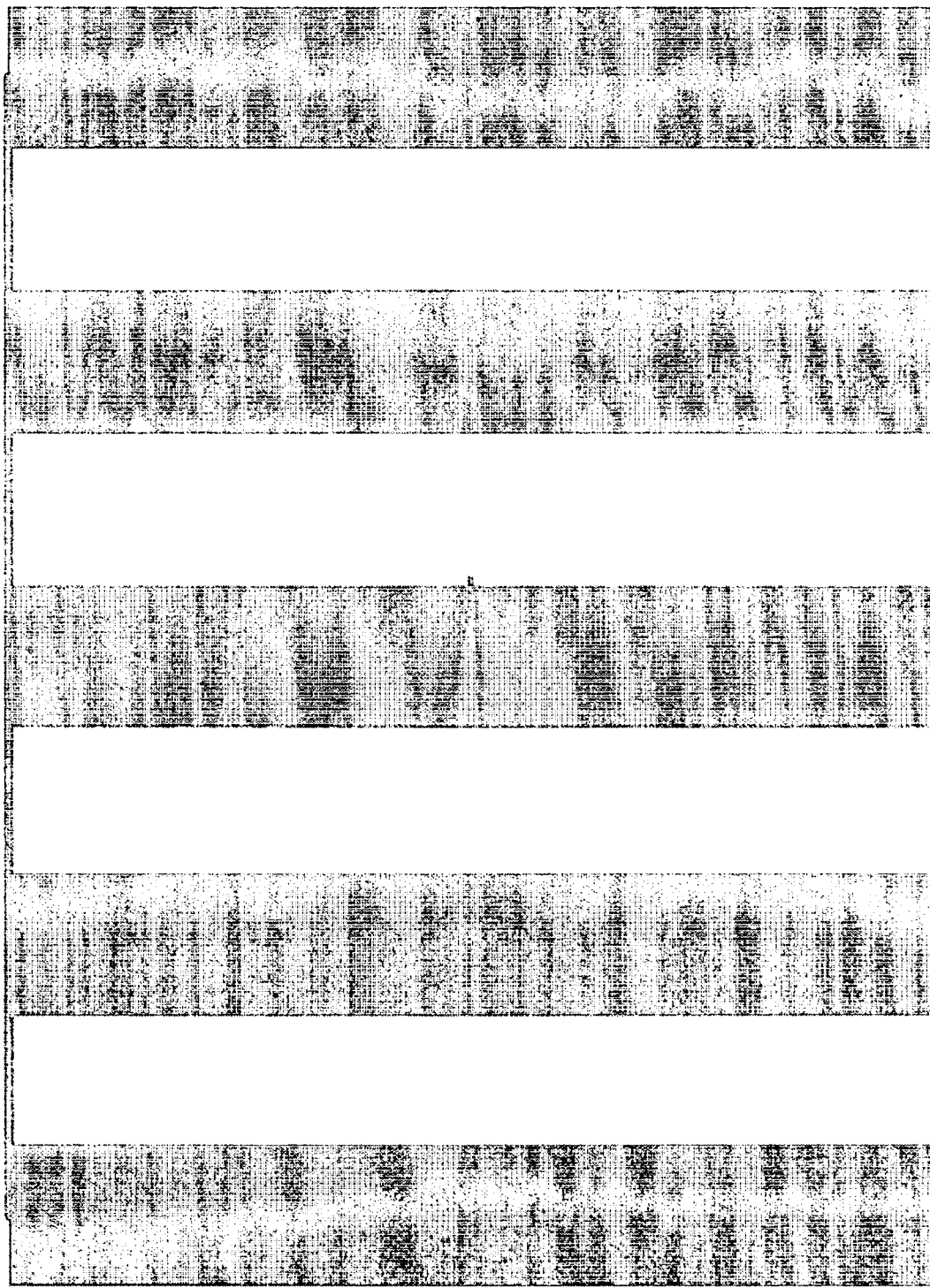
Figure 3C:
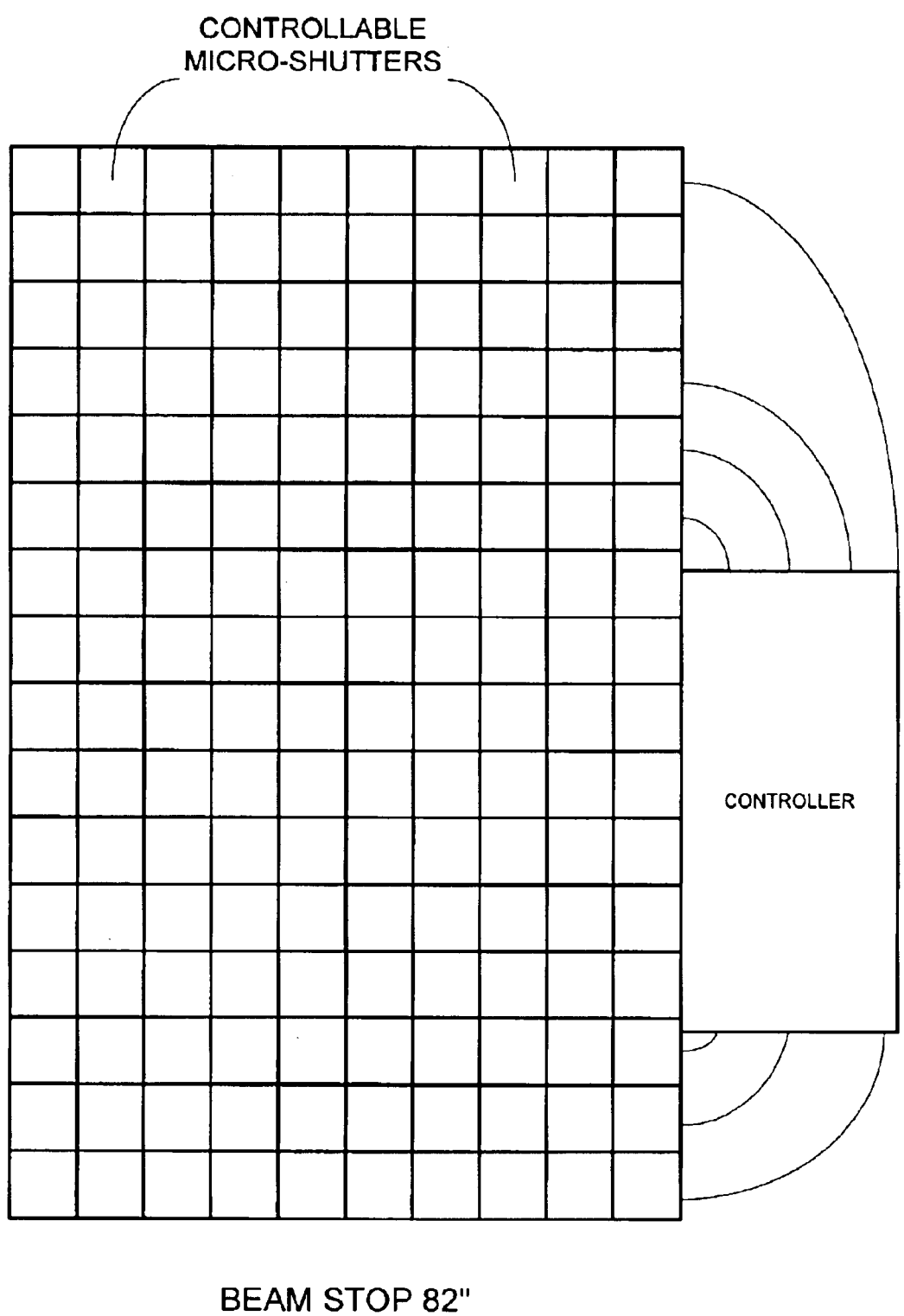

FIG. 3A illustrates beam stop 82 that defines a collection zone that corresponds to a single arc-shaped estimated fringe. FIG. 3B illustrates beam stop 82" that defines a collection zone that corresponds to multiple linear fringes. FIG. 3C illustrates an adjustable beam stop 81' that has multiple controllable shutters that may be controlled to define a collection zone.

It is noted that either one of systems 20–20" may include multiple detectors that are positioned at various locations to define multiple collection zones, thus providing more information about the interference patterns and accordingly to facilitate improved defect detection capabilities. At least some of the detectors may be positioned (and the beam stop may be configured) to detect bright fringes. These detectors may have distinct sensitivity and/or dynamic range than the detectors that are designed to collect dark fringes.

Once the interference pattern is estimated (either by calculation or by measurement or by a combination of both), usually assuming a non-defective wafer, a detector and a beam stop may be positioned such as to define a collection zone. It is noted that the measurement may be performed when the first and second spot interact with a repetitive pattern of the wafer. If is further noted that multiple measurements iteration may be executed to provide a better/finer estimation of the interference pattern. Changes of the dark fringe intensity as well as displacement of the dark fringe may indicate the presence of a defect.

Light that passes through beam stop 82 is received by a detector 84, preferably a photomultiplier tube (although detectors of other types may also be used). Typically, detector 84 is connected to a processor 38 that comprises a general-purpose computer, with suitable software and front-end circuits for interacting with detector 58 and other elements of system 20. The processor 38 may also include dedicated image processing capabilities. Preferably, processor 38 also controls transducer 28 so as to adjust the properties of traveling lenses 30 and 32 as required.

Figure 4:
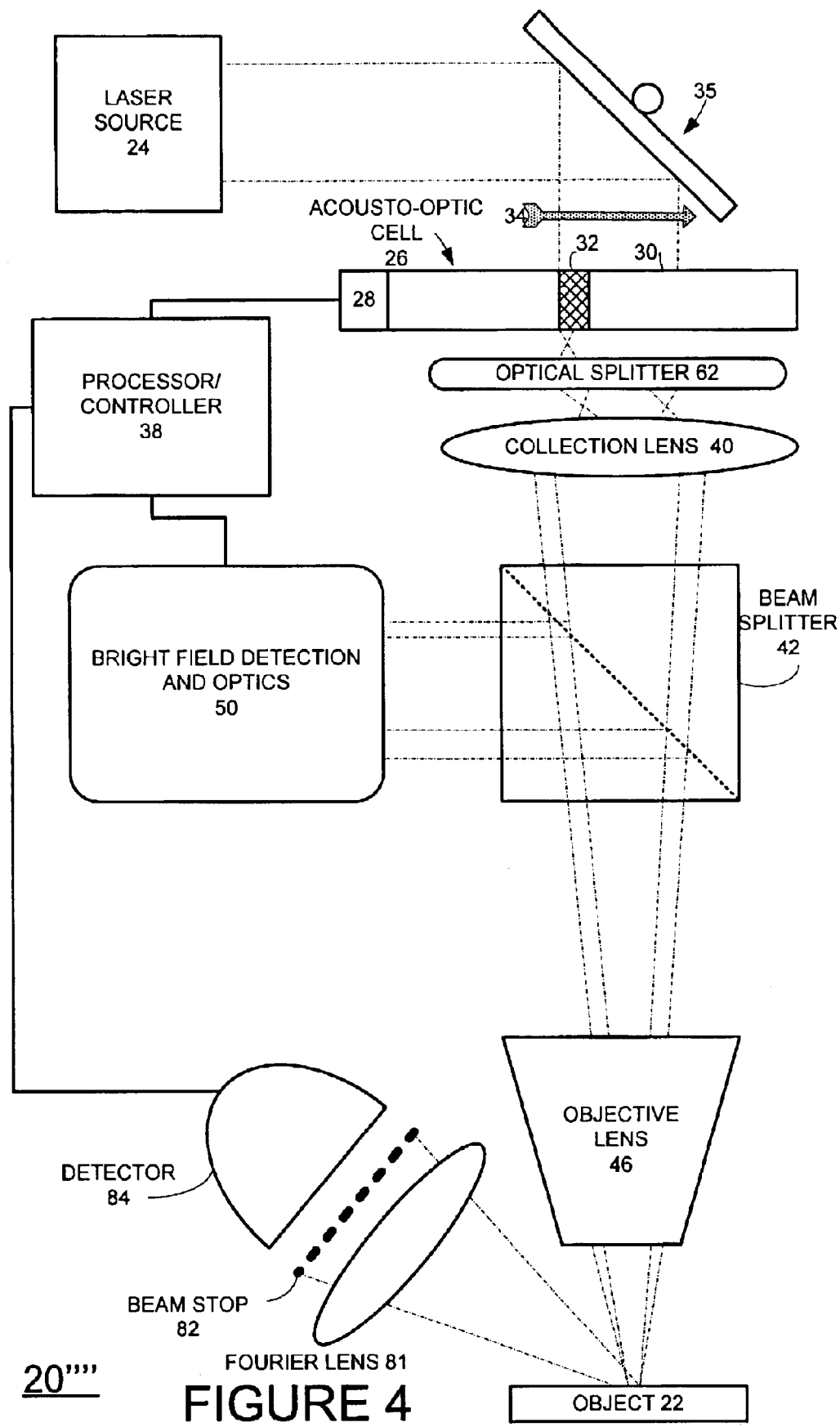

FIG. 4 is a schematic side view of system 20"", in accordance with an alternative embodiment of the present invention. In this embodiment, transducer 28 generates only a single traveling lens 30 in Bragg cell 26. In order to generate both spots 48 and 50 on sample 22, an optical splitter 62, typically a diffractive element, such as a transmission grating, is inserted in the beam path as shown.

Two closely spaced diffraction orders provide the two spots. In other respects, the operation of this embodiment is substantially the same as the embodiments of FIGS. 1A–1C. Of course, when only the single traveling lens is used, as in the embodiment of FIG. 4, the relative positions and phases of spots 48 and 50 cannot be so readily adjusted.

Figure 5:
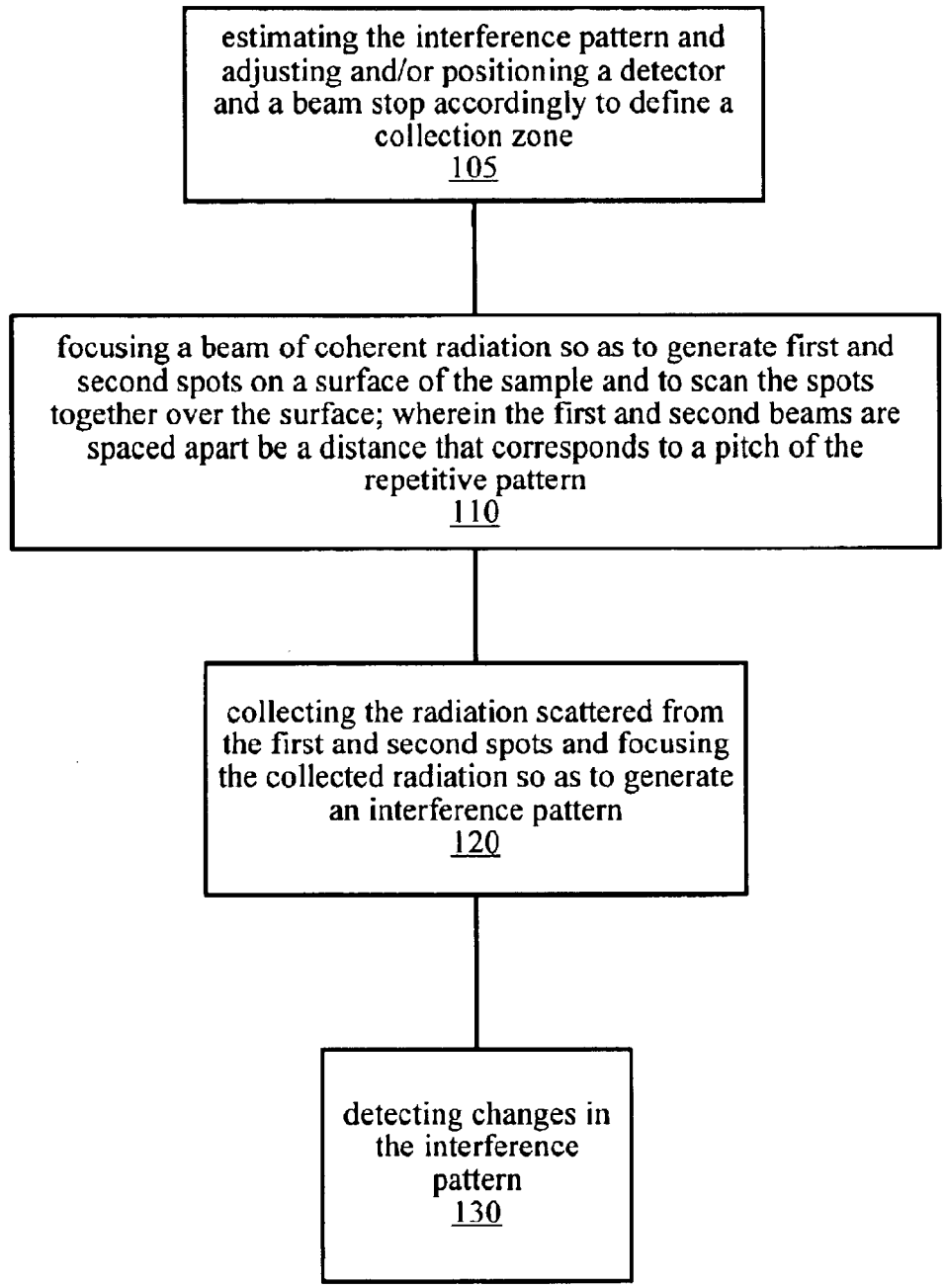
FIG. 5 is a flow chart that schematically illustrates a method for dual-spot scanning, in accordance with an embodiment of the present invention.

FIG. 5 is a flow chart of method 100 for dual-spot scanning and detection. Method 100 starts by step 110 of focusing a beam of coherent radiation so as to generate first and second spots on a surface of the sample and to scan the spots together over the surface. The first and second beams are spaced apart by a distance that corresponds to a pitch of the repetitive pattern. Preferably this distance is substantially equal to a multiple integer of the pitch of the repetitive pattern. Referring to FIGS. 1A–1C, the beams are generated and focused by laser source 24, acousto-optic Bragg cell 26, collection lens 40, beam-splitter 42, telescope 44 and objective lens 46.

Step 110 is followed by step 120 of collecting the radiation scattered from the first and second spots and focusing the collected radiation so as to generate a pattern of interference fringes. Referring to FIG. 1A the collection path includes Fourier lens 81. Referring to FIGS. 1B and 1C the collection optics include objective lens 46, telescope 44, mirror 43 (and mirror 45, in the case of FIG. 1C) and dark field optics 78.

Step 120 is followed by step 130 of detecting changes in the pattern of the interference fringes. The changes are detected by processing the detection signals provided by dark field detectors such as detector 84. Preferably this step includes positioning a beam stop, such as beam stop 84, so that in a reference position of the fringes, the beam stop blocks the bright fringes, and measuring the radiation that passes through the beam stop as the spots are scanned over the surface. It is noted that the processing may include outputting an alarm signal whenever the detected intensity is above a predefined threshold. The alarm signal may be used for generating a defect map.

Method 100 may further include a preliminary step 105 of estimating the interference pattern (and especially the location of at least one fringe), either by calculation or by measurement or by a combination of both, and either adjusting and/or positioning a detector and a beam stop accordingly to define a collection zone.

It will be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus for optical assessment of a sample having a repetitive pattern, comprising:

a radiation source, adapted to generate a beam of coherent radiation;

traveling lens optics, adapted to focus the beam so as to generate first and second spots on a surface of the sample and to scan the spots together over the surface; wherein the first and second spots are spaced apart by a distance that corresponds to a pitch of the repetitive pattern;

collection optics, positioned to collect the radiation scattered from the first and second spots and to focus the collected radiation so as to generate an interference pattern; and a detection unit, adapted to detect changes in the interference pattern.

2. Apparatus according to claim 1, wherein the traveling lens optics comprise an acousto-optic Bragg cell and an acoustic transducer coupled to the cell so as to produce first and second frequency-modulated acoustic pulses, which travel along a length of the cell, such that when the beam of radiation passes through the cell, it is focused by the first and second pulses so as to generate and scan the first and second spots, respectively.

3. Apparatus according to claim 2, wherein the transducer is controllable so as to vary a relative timing and phase of the acoustic pulses, thereby controlling a spacing and relative phase of the first and second spots.

4. Apparatus according to claim 1, wherein the detection unit comprises:

a detector, which is adapted to generate an output signal responsive to the change in the pattern of the interference fringes; and a signal processor, which is coupled to receive and process the output signal so as to determine a presence of a defect.

5. Apparatus according to claim 1, wherein the interference pattern comprises bright and dark fringes that alternate with a fringe period, and wherein the collection optics comprise a beam stop, which is configured and positioned so that in a reference position of the fringes, the beam stop blocks the bright fringes from impinging on the detector.

6. Apparatus according to claim 1, wherein the traveling wave optics are adapted to focus the beam so that the spots have a predetermined spot width, and whereas the spot width are smaller than the pitch of the repetitive pattern.

7. Apparatus according to claim 1 wherein the first and second beams are spaced apart by a distance that is a multiple integer of the pitch of the repetitive pattern.

8. Apparatus according to claim 1 wherein the beam stop is operable to adjust a collection zone defined by the beam stop.

9. Apparatus according to claim 1, wherein the traveling lens optics comprise: an acousto-optic Bragg cell and an acoustic transducer coupled to the cell so as to produce a frequency-modulated acoustic pulse, which travels along a length of the cell, such that when the beam of radiation passes through the cell, it is focused and scanned by the acoustic pulse; and an optical splitter, which is configured to split the beam that is focused and scanned by the acoustic pulse in the Bragg cell, so as to generate the first and second spots on the surface.

10. Apparatus according to any claim of claims 1–9 whereas the first and second spots are smaller than the pitch of the repetitive pattern.

11. A method for optical assessment of a sample, comprising: focusing a beam of coherent radiation so as to generate first and second spots on a surface of the sample and to scan the spots together over the surface; wherein the first and second beams are spaced apart be a distance that corresponds to a pitch of the repetitive pattern; collecting the radiation scattered from the first and second spots and focusing the collected radiation so as to generate an interference pattern; and detecting changes in the interference pattern.

12. A method according to claim 11, wherein focusing the beam of coherent radiation comprises applying first and second frequency-modulated acoustic pulses to an acousto-optic Bragg cell, so that the first and second pulses travel along a length of the cell, such that when the beam of radiation passes through the cell, it is focused by the first and second pulses so as to generate and scan the first and second spots, respectively.

13. A method according to claim 12, wherein applying first and second frequency-modulated acoustic pulses comprises varying a relative timing and phase of the acoustic pulses so as to control a spacing and relative phase of the first and second spots.

14. A method according to claim 11, wherein detecting the shift comprises generating an output signal responsive to the change in the pattern of the interference fringes.

15. A method according to claim 11, wherein the interference fringes comprise bright and dark fringes that alternate with a fringe period, and wherein detecting the change comprises positioning a beam stop so that in a reference position of the fringes, the beam stop blocks the bright fringes, and measuring the radiation that passes through the beam stop as the spots are scanned over the surface.

16. A method according to claim 11, wherein focusing the beam comprises: applying a frequency-modulated acoustic pulses to an acousto-optic Bragg cell, so as to produce a frequency-modulated acoustic pulse, which travels along a length of the cell, such that when the beam of radiation passes through the cell, it is focused and scanned by the acoustic pulse; and splitting the beam that is focused and scanned by the acoustic pulse in the Bragg cell, so as to generate the first and second spots on the surface.

17. A method according to any claim of claims 11–16 whereas the first and second spots are smaller than the pitch of the repetitive pattern.

18. A method according to step 11 wherein the step of detecting changes in the interference pattern comprises detecting changes in an intensity of light detected by detection unit.

* * * * *